United States Patent [19]

Guillou et al.

[11] Patent Number: Plant 7,352

[45] Date of Patent: Oct. 9, 1990

[54] VARIETY OF GERANIUM NAMED MIMI

[75] Inventors: Jacques Guillou; Bernard Guillou; Maurice Guillou, all of Saint-Malo, France

[73] Assignee: Etablissement Guillou Freres Jacques, Bernard et Maurice, France

[21] Appl. No.: 359,877

[22] Filed: May 31, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Webb, Burden, Ziesenheim & Webb

[57] ABSTRACT

A new and distinct ivy Geranium variety shows great improvement over the current commercial counterpart "Beauty of Eastbourne". While somewhat similar in color, this new variety is much more vibrant. A much fuller plant habit; more cuttings which root more quickly and a much greater tolerance to heat are all characteristics which allow Mimi to be the more outstanding ivy Geranium.

1 Drawing Sheet

BACKGROUND OF THE NEW PLANT

The present invention comprises a new and distinct cultivar of *Pelargonium*×*peltatum* known by the varietal name Mimi (Oglevee Ltd. No. 7044, French No. 541 Guidonal). The new variety was discovered in a selective breeding program by Messrs. Jacques, Maurice and Bernard Guillou. The new variety is a selection from the crossing of No. 14 Bouvet×No. 12. The new variety is more floriferous than its parentage.

The new cultivar was discovered in 1986 at 55 rue Godard, 35400 Saint-Malo, France, was first asexually reproduced by cuttings during 1987 at Saint-Malo, France, and more recently has been repeatedly asexually reproduced by cuttings at Oglevee Ltd. in Connellsville, Pa. It has been found to retain its distinct characteristics through successive propagations.

The new cultivar, when grown in a glass greenhouse in Connellsville, Pa., use full light, 60° F. night temperature, 68° F. day temperature, 71° F. vent temperature, and grown in a soilless media with constant fertilizer of 200–250 parts per million nitrogen and potassium, has a response time from a rooted cutting to a flowering plant in a four inch (10 cm) pot of six weeks.

DESCRIPTION OF THE DRAWING

The accompanying drawing illustrates a new cultivar, the color being as true as possible with color illustrations of this type.

DESCRIPTION OF THE NEW PLANT

The following detailed description set forth the characteristics of the new cultivar. The data which define these characteristics were collected from asexual reproductions carried out by Oglevee Ltd. in Connellsville, Pa. The plants were started as rooted cuttings which were potted on Aug. 1, 1988 and flowered on Sept. 15, 1988. Three 10 cm pots were potted into a 26 cm hanging basket and maintained until Mar. 23, 1989 when the color readings were taken. The plant histories were taken of plants blossomed under full light in a greenhouse and color readings were taken indoors under 200–220 foot candles of cool white fluorescent light. Color references are primarily to the R.H.S. Colour Chart of The Royal Horticultural Society of London.

THE PLANT

Classification:
- *Botanical.*—*Pelargonium*×*peltatum.*
- *Commercial.*—Ivy Geranium Mimi (#7044).

Form: Cascading mound habit.

Height: 20–25 cm above media surface.

Growth: Free branching, free and early flowering; upright mound with cascading side growth.

Strength: Holds an upright mound shape while allowing outer branches to cascade over the sides of the pot.

Foliage: Stalked leaf attachment; very faint zone present.

Leaves:
- *Size.*—5.5–7 cm across.
- *Shape.*—Reniform, cordate base.
- *Margin.*—Pedately lobed.
- *Texture.*—Smooth; slightly reflective; slightly pubescent.
- *Color.*—Top: Green Group 137B; Bottom: Yellow-Green Group 146B.
- *Ribs and veins.*—Palmate venation; Color: Yellow-Green Group 146C.

Petioles: 2.6–6 cm in length.
- *Color.*—Yellow-Green Group 146B.

Stem:
- *Color.*—Yellow-Green Group 146C.
- *Internodes.*—2.5–6 cm in length.

THE BUD

Shape: Upright; hemispherical cluster.

Size: 2.5–3 cm across.

INFLORESCENCE

Blooming habit: Continuous; upright; semi-hemispherical.

Size: 6.5–7 cm across when fully opened.

Borne: Florets on pedicel; pedicel on peduncle; Umbel sets directly above foliage canopy.

Florets:
- *Form.*—Flat to slightly cupped.
- *Color.*—Top: Red Group 52A with a blotch of Red-Purple Group 66B on upper two petals. Bottom: Outer edge Red Group 50A shading to a lighter Red Group 49A in the center.

*Petals.*—10–12 in number, separate, not united; margin entire.

*Floret size.*—5–5.5 cm across when fully open.

*Texture and appearance.*—Smooth; from a distance the bloom color appears as a rich rose with the upper petals having some darker veining and a blotch.

Petaloids:

*Quantity.*—3–5.

*Shape.*—Elongated, twisted, some with anther attached.

*Color.*—Red Group 52A.

Pedicel: 1.5–2 cm in length.

*Color.*—Yellow-Green Group 146B.

Peduncle: 7–11 cm in length.

*Color.*—Yellow-Green Group 146B; arises from the node opposite the leaf petiole.

Disease resistance: Not known.

Lasting Quality: Mimi is very heat tolerant with both the bloom and foliage holding up very well.

REPRODUCTIVE ORGANS

Stamens:

*Anthers.*—2–3 mm in length.

*Filaments.*—9–10 mm in length; white at the base to light pink at the tip.

*Pollen: Golden brown.*

Pistils:

*Number.*—One.

*Length.*—9–10 mm.

*Stigma.*—5 or 6 parted; Red-purple.

*Style.*—3–4 mm in length; white.

Ovaries: Superior; very pubescent; pale green; 4–6 mm in length, 3 mm across.

Fruit: Occasional fruit observed.

GENERAL CHARACTERISTICS

This new and distinct ivy Geranium variety shows great improvement over the current commercial counterpart "Beauty of Eastbourne" which has slightly more blue-red hues.

Although somewhat similar in color, this new variety is much more vibrant. A much fuller plant habit; more cuttings which root more quickly and a much greater tolerance to heat are all characteristics which allow Mimi to be the more outstanding ivy Geranium.

We claim:

1. A new and distinct variety of ivy Geranium plant as shown and described herein and characterized by substantive improvement over the current commercial counterpart "Beauty of Eastbourne", being much more vibrant, a much fuller plant habit; more cuttings which root more quickly and a much greater tolerance to heat.

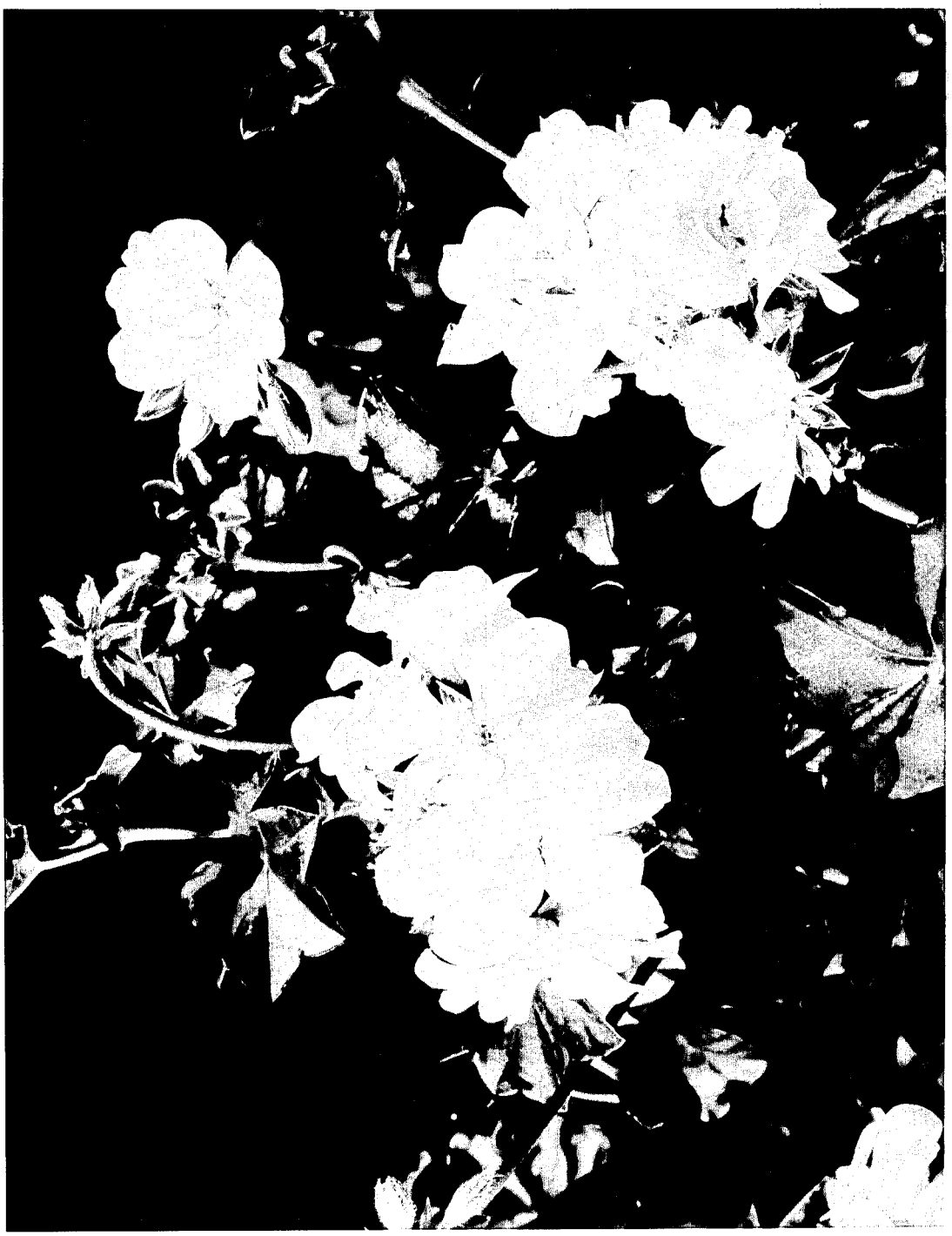

* * * * *